United States Patent [19]

Bessman

[11] 4,311,050
[45] Jan. 19, 1982

[54] RESERVOIR FOR MEDICAMENTS

[76] Inventor: Samuel P. Bessman, 2025 Zonal Ave., Los Angeles, Calif. 90033

[21] Appl. No.: 195,090

[22] Filed: Oct. 8, 1980

Related U.S. Application Data

[63] Continuation-in-part of Ser. No. 69,765, Aug. 27, 1979, abandoned.

[51] Int. Cl.³ .............. G01F 19/00; B65D 85/02
[52] U.S. Cl. .................. 73/427; 116/308; 128/272; 206/303
[58] Field of Search ............ 116/227, 308, 318, 307; 73/149, 427; 128/213 R, 216, 272, 272.3, 260, 214.4; 206/303

[56] References Cited

U.S. PATENT DOCUMENTS

| | | | |
|---|---|---|---|
| 2,652,922 | 9/1953 | Schweich | 206/303 X |
| 2,662,400 | 12/1953 | Weiner et al. | 73/149 |
| 2,711,734 | 6/1955 | Moe | 128/276 |
| 3,042,086 | 7/1962 | Winchell | 128/272 X |
| 3,561,445 | 2/1971 | Katerndahl | 128/214.4 |
| 3,788,322 | 1/1974 | Michaels | 128/272 X |
| 3,906,794 | 9/1975 | Shotmeyer | 73/302 X |
| 3,921,806 | 11/1975 | Wawracz | 116/308 |
| 3,963,380 | 6/1976 | Thomas, Jr. | 417/412 X |
| 4,154,098 | 5/1979 | Pelletier | 73/149 |
| 4,159,720 | 7/1979 | Burton | 128/213 R |
| 4,191,181 | 3/1980 | Franetzki et al. | 128/213 R |
| 4,246,789 | 1/1981 | Olds | 73/427 X |

*Primary Examiner*—Daniel M. Yasich
*Attorney, Agent, or Firm*—Fidelman, Wolffe & Waldron

[57] ABSTRACT

A reservoir for a pharmacologic delivery system wherein liquid level changes are readable visually to an accuracy of within five microliters. The reservoir is formed as a spirally coiled tubular member disposed between a pair of plate members spaced apart by one or more concentric rims. The tubular member forms a continuous spiral coil between the plate members, one tube end porting through one of the plates at the center thereof and the other tube end porting at the plate circumference. Transparent materials of construction are employed, as appropriate, and one of the plate members may have indicia thereon for assisting the viewer to measure volume changes inside the reservoir.

11 Claims, 7 Drawing Figures

U.S. Patent   Jan. 19, 1982   Sheet 1 of 2   4,311,050
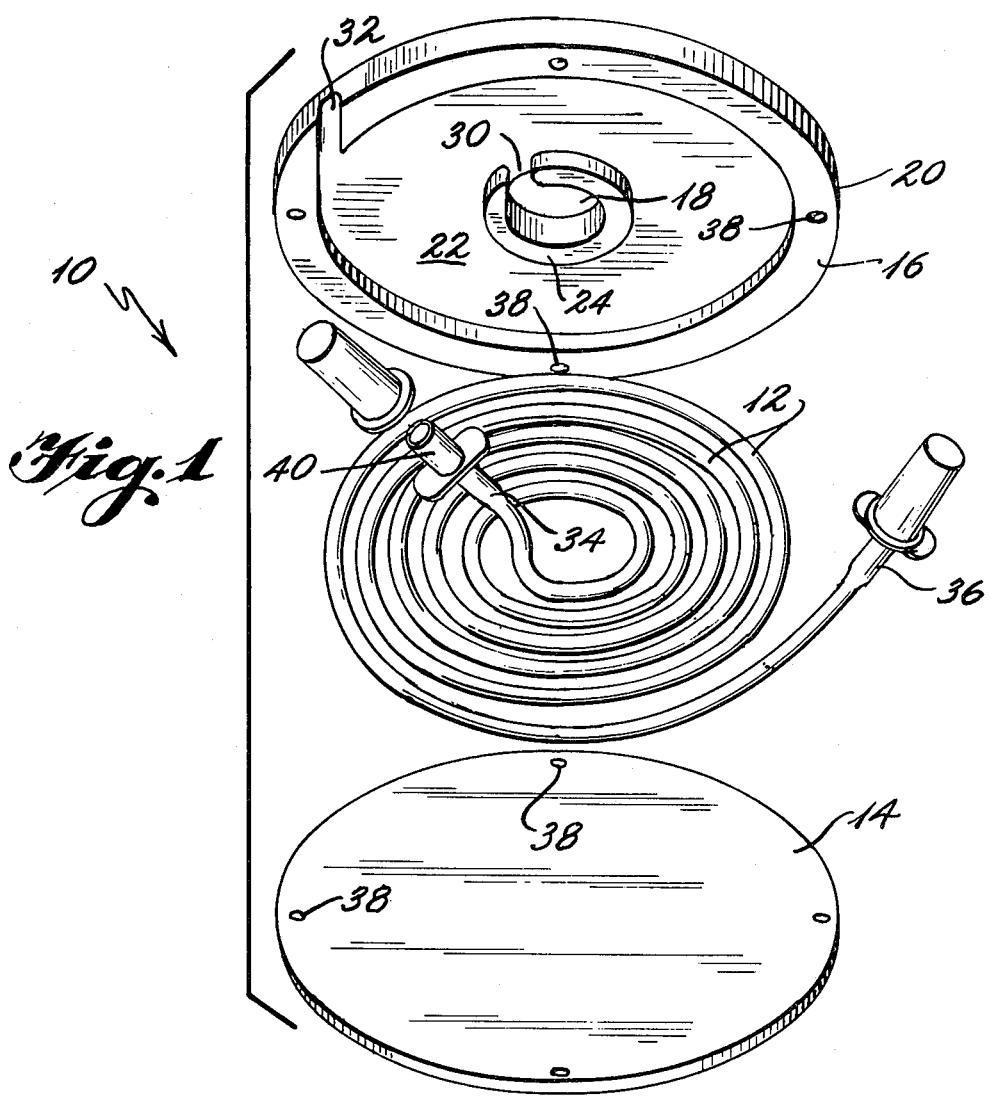
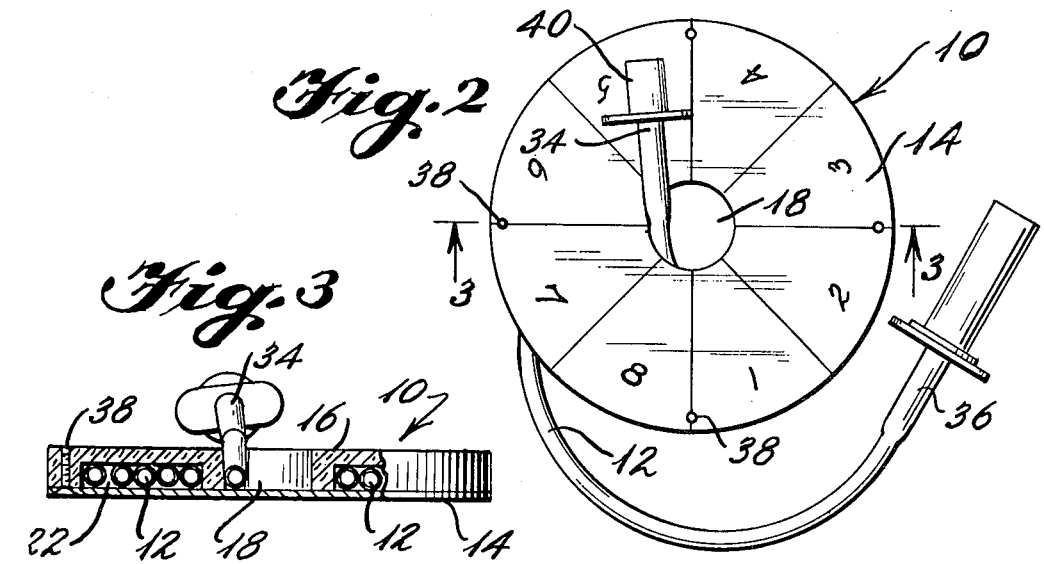
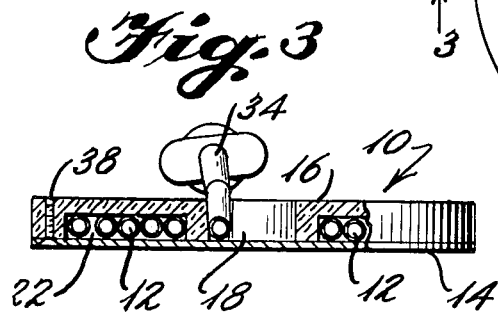

RESERVOIR FOR MEDICAMENTS

CROSS-REFERENCE TO RELATED APPLICATIONS

This application is a continuation-in-part of patent application Ser. No. 069,765 filed Aug. 27, 1979 and now abandoned.

FIELD OF THE INVENTION

This invention relates to a visible reservoir adapted for a pharmacologic delivery system.

BACKGROUND OF THE INVENTION

Some medicants, notably insulin, are administered in small quantities at regular intervals. To reduce the disadvantages inherent in administration of relatively large medicament doses intermittently, the suggestion has been made to employ a micropump so that only microliter quantities of the medicament are introduced at any one moment. The amounts delivered are frequently measured by a reading of the pumping rate, e.g., by counting the pump pulses of the micropump delivery system (Reference is made to U.S. Pat. No. 3,963,380 for detailed discussion of a micropump adapted to deliver small quantities of medicament.)

Use of a micropump for medicament delivery essentially presupposes that the medicament is removed from a reservoir. Manifestly, a reservoir whose level can be read directly with great accuracy would be a desirable adjunct for micropump delivery of a medicament.

OBJECTS OF THE INVENTION

The object of this invention is to provide an indicating reservoir wherein quantity differences of less than 10 microliters, preferably less than 5 microliters can be ascertained readily.

SUMMARY OF THE INVENTION

The reservoir of the present invention utilizes a spirally coiled partially or fully transparent or translucent tubular member framed by or between two plate members, at least one of which is transparent. The transparent plate member may be marked with indicia to determine liquid volume changes in the reservoir as by noting the position of the liquid meniscus within the tube. In one embodiment of the invention, the transparent plate may be marked out in quadrant or subquadrant segments. To read volume changes in the reservoir, the number of tube coils, counted to or from the center constitutes a gross measure of a change in volume and the angular difference between successive positions of the liquid miniscus, or liquid level between readings constitutes the fine measure. Since the coil spirals out from a central point, the length of coil per ten varies which causes the contained volume in each coil to change substantially in a mathematically predictable fashion from one coil to the next. A calibration chart may be desirable to correlate volume change with the number of tube coils.

In another embodiment of the invention, the transparent plate is marked with indicia in a spiral arcuate pattern conforming to and superposed on the spiral pattern formed by the coiled tube. The indicia define equal lengths of tube arc thus allowing volume changes to be read directly in standard volume units.

In one preferred embodiment, both top and bottom plates include a spiral, hemispherical groove on one fan thereof. When the plates are assembled in mating position, the superposed hemispherical grooves form a continuous, spiral tubular channel, one end of the channel porting through one, preferably the top one, of the plates and the other channel end porting at the plate circumference.

A tube about 10 mm square cross-sectional area requires 10 cm of tube per ml of liquid; 50 cm of tubing can be coiled into a disk less than 10 cm in diameter. Such a coiled tube reservoir holding of 5 cc of liquid is compatible with the size of a portable micropump. Changes in reservoir volume of 5 microliters (0.005 ml) or less can be ascertained in the reservoir and measured.

BRIEF DESCRIPTION OF THE DRAWINGS

FIG. 1 is an exploded diagrammatic view of one embodiment of the reservoir.

FIG. 2 is a plan view of the reservoir of FIG. 1.

FIG. 3 is a sectional view of the reservoir taken along line 3—3 on FIG. 2.

DETAILED DESCRIPTION OF THE INVENTION

Figure 4:
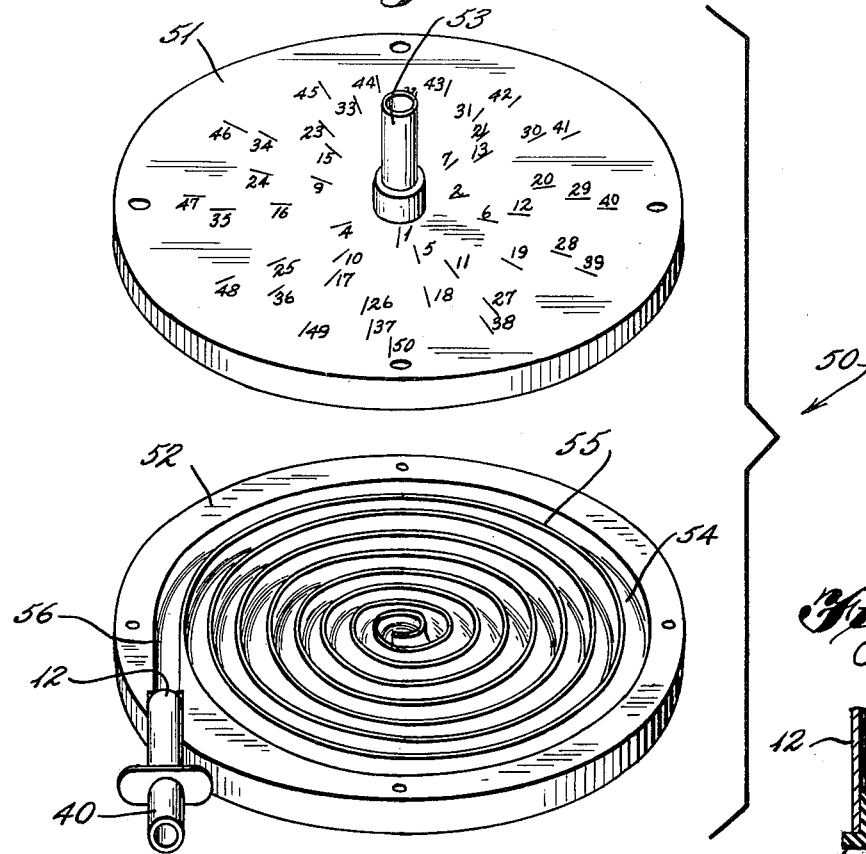
FIG. 4 is a partially dissembled view of a second embodiment of the invention.

Referring first to FIGS. 1-3, it may be seen that reservoir 10 is made up of a (coiled) tube 12, a face sheet or plate 14 and a disk 16. The disk is formed with a central opening or aperture 18. One face of disk 16 contains an annular compartment or recess 22 formed by inner rim 24, and outer rim 20. The tube 12 is coiled around the inner, generally circular, rim 24 and fills compartment 22. An inner rim slit or aperture 30 and an outer rim slit or aperture 32 allow the tube ends 34, 36 to extend into and out of compartment 22 through the rims 20, 24 and be largely in the plane of disk 16.

The reservoir 10 is assembled by inserting tube end 34 through the inner rim slit 30, then coiling the tube 12 inside compartment 22 filling same with coils and thereafter leading the free tube end 36 through outer rim slit 32. Thereafter face plate or sheet 14 is applied and secured to disk 16, e.g., by screws placed in holes 38 in outer rim 26, or if desired by an adhesive.

The tube ends 34 and 36 are provided with fittings appropriate to the intended use for reservoir 10. For example, the tube ends may be provided with male Luer fittings 40 of the type commonly used on hypodermic needles. After reservoir 10 is filled an anti-bacterial filter would be fitted on whichever tube end is open to the atmosphere to filter air drawn into the reservoir as it empties.

In use, the tube coil 12 of reservoir 10 is filled with a liquid medicament as, for example, insulin. One tube end is connected to the suction side of a micropump as by connecting a male Luer fitting on the tube end to a female Luer fitting on the pump entry. A filter is then coupled to the other tube end. The output of the pump delivers medicament to the patient.

Action of the pump draws liquid medicament from tube 12 of reservoir 10 causing the liquid miniscus or liquid level to move or travel through the tube and allowing observation of the position of the liquid miniscus relative to the indicia provided on plate 14. As is illustrated in FIG. 2, the outside face of plate 14 may be marked off in quadrants and lesser segments of the reservoir, eight segments numbered 1-8 being illustrated by the drawing. A measure of the medicament volume drawn from the reservoir by the pump may be obtained by locating the liquid meniscus and counting the number of tube coils from the meniscus to the reservoir center to obtain a gross measure of volume change. Angular position of the meniscus as determined by the meniscus position relative to the indicia on plate 14 provides a fine measure of volume change.

Tube 12, disk 16 and face plate 14 are all illustrated as transparent materials capable of being autoclaved, of which a considerable number are available commercially. No need exists, however, for both face plate 14 and disk 16 to be transparent; one is enough, as long as the liquid level in the coils and the indicia are visible from the outside.

Allusion has already been made to the small size of reservoir 10. In one preferred embodiment constructed and marked off as illustrated herein, six coils of 3 mm I.D. (internal diameter) tubing were contained in the compartment of a 3" diameter disk with a 0.5" center opening ¼" in depth. Storage volume was 3.5 cc. Visual measurement of volume changes accurate to about 5 micro liters (0.005 ml) could be made. This particular reservoir served well in test studies wherein insulin was administered to dogs using the micropump structure described by U.S. Pat. No. 3,963,380.

Figure 5:
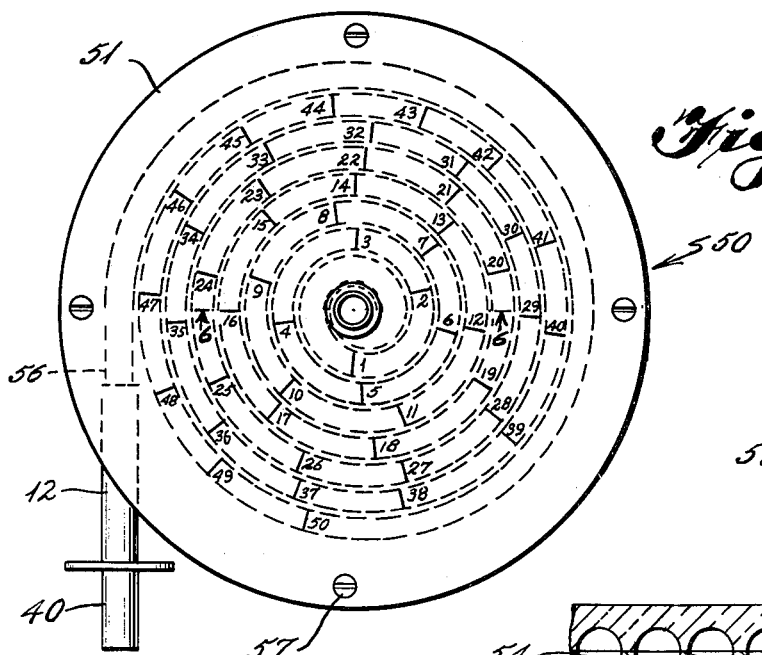
FIG. 5 is a plan view of the reservoir of FIG. 4.
Figure 6:
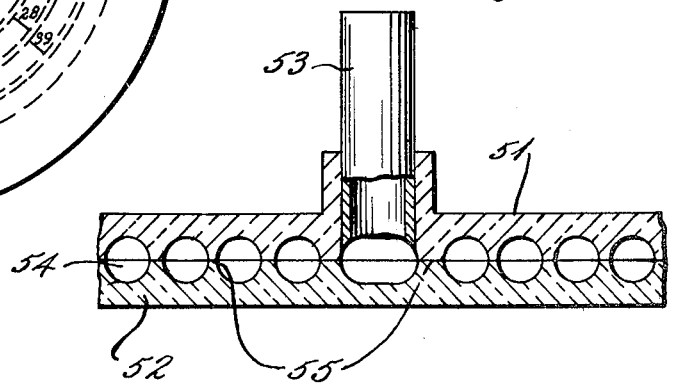
FIG. 6 is a partial sectional view taken generally along line 6—6 of FIG. 5.

Referring now to FIGS. 4 to 6, there is shown another embodiment of the invention which allows volume changes in the reservoir to be read in standard units. The reservoir shown generally at 50 includes an upper plate 51 and a lower plate 52. Disposed in the center of upper plate 51 and extending perpendicularly thereto is connection nipple 53 which communicates to the bottom side of plate 51. Upper plate 51 and lower plate 52 are formed with a continuous spiral hemispherical groove 54 defined by a continuous spiral groove wall 55 beginning at the center of plate 52 and terminating in a tangential extension 56 forming an exit port through the rim of plate 52. Groove 54 is dimensioned so that its assembled diameter is essentially identical to the internal diameter of tubular member 12 illustrated in FIG. 1. One end of the tubular member formed by the superposed grooves and groove walls terminates in a suitable fitting, typically a male Luer fitting 40, adjacent the plate rim as is shown while the other end of the tube is connected to and communicates with nipple 53. In use, the male Luer fitting would lock into a female fitting attached to the pump.

Figure 7:
FIG. 7 depicts a tubing end connection.

In an alternative, and in some cases a preferred embodiment, a rubber dam illustrated in FIG. 7 is substituted for male Luer fitting 40. In this embodiment the pump would be fitted with a hypodermic needle pointing outwardly and the reservoir would be coupled to the pump by inserting the needle through the dam. Use of the needle-dam coupling method provides a more positive means for avoiding introduction of air bubbles into the system that does the Luer connectors.

Upper plate 51 is provided with indicia, suitably radially scribed line segments, arranged spirally and positioned to be superposed over the spiral groove 54 when the reservoir is assembled in the manner illustrated in FIG. 5. Because the internal diameter of the tubular member formed by the superposed grooves and groove walls is both known and constant, the arcuate distance between adjacent indicia can be selected to provide a readout directly in standard volume units, e.g., microliters. In the embodiment illustrated, the upper plate 51 is divided into fifty units numbered 1-50 as shown in FIGS. 4 and 5. Each unit includes the same arcuate length and so represents an equal volume.

FIG. 6 is a partial sectional view taken along lines 6—6 of FIG. 5 and more clearly illustrates the grooves 54 and groove walls 55. As may be appreciated from this view, plates 51 and 52 may be formed from a suitable, autoclavable plastic material by injection molding or similar techniques. In one preferred construction technique, the two plates are molded or cast from plastic as matching top and bottom sections having indices molded into the top plate. The top and bottom plates 51, 52 are held in an assembled position by screws 57, (FIG. 5) adhesives, or other suitable connecting means. A filter plug may be inserted within nipple 53 to insure that air drawn into tube 12 as liquid is removed therefrom by action of the pump is free from all suspended bodies.

FIG. 7 illustrates an alternative tube end fitting which may be used as described previously and with all of the other different embodiments of the invention. In this embodiment, a rubber dam 61, of the type used on serum vials, is inserted in a press fit within the end of tube 12. A standard hypodermic needle 62 is then inserted through dam 61 to provide a fluid passage. Needle 62 may be attached to tubing 63, leading to the pump suction inlet, by any conventional technique or the needle base may be connected directly to the pump through Luer type fittings or the like.

Although the construction of the reservoir has been described in terms of circular plates and rims, it should be appreciated that neither rims nor plates need be true circles. They could, for example, be ellipses. Thus, within the context of this invention it should be appreciated that the term "circular" includes circles, ellipses and like closed curves within its intent.

I claim:

1. A reservoir for a liquid medicament adapted to visual indication of microliter changes in medicament volume which comprises:
    a pair of generally circular plate members, at least one of which is transparent;
    a spirally coiled, transparent, medicament holding tubular member disposed in a planar configuration between said plate members, one end of said tubular member porting in a center opening in one of said plate members and the other end of said tubular member porting at the circumference of said plate members;
    means disposed on one of said ends of said tubular member and adapted for attachment to liqud withdrawal means, and
    indicia on said transparent plate member, said indicia arranged to provide a measure of medicament volume change within the reservoir as medicament is drawn therefrom.

2. The reservoir of claim 1 wherein said indicia comprise a multiplicity of radial lines dividing the circular plate area into subquadrants.

3. The reservoir of claim 1 wherein one of said plate members is transparent.

4. The reservoir of claim 1 wherein one of said members includes an upstanding nipple disposed at the center opening thereof and communicating with said one end of said tubular member.

5. The reservoir of claim 1 wherein said indicia comprise a plurality of radially scribed line segments arranged spirally and superposed over said spirally coiled tubular member.

6. The reservoir of claim 5 wherein the arcuate distance between adjacent line segments is selected to provide a readout in standard volume units.

7. A reservoir for a liqud medicament adapted to visual indication of microliter changes in medicament volume which comprises:

a pair of generally circular plate members, at least one of which is transparent, the mating sides of said plate members defining a continuous spiral tubular member formed by a continuous spiral hemispherical groove and a continuous spiral wall beginning at the center and terminating at the circumferential wall, one end of said tubular member porting in a center opening in one of said plate members and the other end of said tubular member porting at the circumference of said plate members;

means disposed on one of said ends of said tubular member and adapted for attachment to liquid withdrawal means, and indicia on said transparent plate member, said indica arranged to provide a measure of medicament volume change within the reservoir as medicament is drawn therefrom.

8. The reservoir of claim 7 wherein one of said plate members is transparent.

9. The reservoir of claim 7 wherein one of said plate members includes an upstanding nipple disposed at the center opening thereof and communicating with said one end of said tubular member.

10. The reservoir of claim 7 wherein said indicia comprise a plurality of radially scribed line segments arranged spirally and superposed over said spiral groove.

11. The reservoir of claim 10 wherein the arcuate distance between adjacent line segments is selected to provide a readout in standard volume units.

* * * * *